US008093446B2

(12) United States Patent  
Knuth et al.

(10) Patent No.: US 8,093,446 B2
(45) Date of Patent: Jan. 10, 2012

(54) FIBROUS ABSORBENT ARTICLES HAVING MALODOR COUNTERACTANT

(75) Inventors: Rosemary F. Knuth, Congers, NY (US); Keith Edgett, Ramsey, NJ (US)

(73) Assignee: Playtex Products, Inc., Westport, CT (US)

( * ) Notice: Subject to any disclaimer, the term of this patent is extended or adjusted under 35 U.S.C. 154(b) by 0 days.

(21) Appl. No.: 10/120,044

(22) Filed: Apr. 10, 2002

(65) Prior Publication Data

US 2002/0188264 A1    Dec. 12, 2002

(51) Int. Cl.
*A61F 13/00* (2006.01)

(52) U.S. Cl. ............... 604/359; 604/360; 604/385.17; 604/904

(58) Field of Classification Search ............ 604/359, 604/360, 904, 385.17
See application file for complete search history.

(56) References Cited

U.S. PATENT DOCUMENTS

| | | | |
|---|---|---|---|
| 3,340,875 A | 9/1967 | Dudley et al. | 128/290 |
| 3,935,862 A | 2/1976 | Kraskin | 128/287 |
| 3,939,838 A | 2/1976 | Fujinami et al. | 128/290 |
| 3,948,257 A | 4/1976 | Bossak | 128/285 |
| 3,949,752 A * | 4/1976 | Van Stee | 604/540 |
| 3,994,298 A * | 11/1976 | Des Marais | 604/363 |
| 4,055,184 A | 10/1977 | Karami | 128/287 |
| 4,217,900 A * | 8/1980 | Wiegner et al. | 604/376 |
| 4,237,591 A | 12/1980 | Ginocchio | 28/121 |
| 4,289,513 A | 9/1981 | Brownhill et al. | 55/387 |
| 4,360,013 A * | 11/1982 | Barrows | 128/832 |
| 4,525,410 A | 6/1985 | Hagiwara et al. | 428/198 |
| 4,529,623 A | 7/1985 | Maggs | 427/227 |
| 4,543,098 A * | 9/1985 | Wolfe et al. | 604/370 |
| 4,547,195 A | 10/1985 | Jackson | 604/359 |
| 4,582,717 A * | 4/1986 | von Bittera et al. | 427/2.31 |
| 4,583,980 A | 4/1986 | Schneider et al. | 604/359 |
| 4,657,808 A | 4/1987 | Maggs | 428/263 |
| 4,724,242 A | 2/1988 | Vassileff | 521/83 |
| 4,743,237 A | 5/1988 | Sweere | 604/358 |
| 4,795,482 A | 1/1989 | Gioffre et al. | 55/75 |
| 4,810,567 A | 3/1989 | Calcaterra et al. | 428/224 |
| 4,826,497 A | 5/1989 | Marcus et al. | 604/359 |
| 4,842,593 A * | 6/1989 | Jordan et al. | 604/360 |
| 4,906,513 A | 3/1990 | Kebbell et al. | 428/198 |
| 5,019,062 A | 5/1991 | Ryan et al. | 604/359 |
| 5,037,412 A | 8/1991 | Tanzer et al. | 604/359 |
| 5,059,282 A * | 10/1991 | Ampulski et al. | 162/111 |
| 5,122,407 A | 6/1992 | Yeo et al. | 428/138 |
| 5,306,487 A | 4/1994 | Karapasha et al. | 424/76.6 |
| 5,342,333 A | 8/1994 | Tanzer et al. | 604/359 |
| 5,364,380 A | 11/1994 | Tanzer et al. | 604/359 |
| 5,407,442 A | 4/1995 | Karapasha | 604/359 |
| 5,429,628 A | 7/1995 | Trinh et al. | 604/359 |
| 5,461,075 A * | 10/1995 | O'Neill et al. | 514/617 |
| 5,580,851 A | 12/1996 | Trinh et al. | 512/4 |
| 5,618,554 A * | 4/1997 | Syverson | 424/431 |
| 5,641,503 A * | 6/1997 | Brown-Skrobot | 424/431 |
| 5,667,750 A * | 9/1997 | Nohr et al. | 264/555 |
| 5,714,445 A | 2/1998 | Trinh et al. | 510/103 |
| 5,716,703 A * | 2/1998 | Payne | 428/378 |
| 5,733,272 A | 3/1998 | Brunner et al. | 604/359 |
| 5,840,744 A * | 11/1998 | Borgman | 514/398 |
| 5,891,123 A * | 4/1999 | Balzar | 604/385.18 |
| 5,891,126 A * | 4/1999 | Osborn et al. | 604/385.17 |
| 5,958,461 A * | 9/1999 | Larsen | 424/614 |
| 5,994,383 A * | 11/1999 | Dyer et al. | 514/390 |
| 6,026,534 A * | 2/2000 | Gonda et al. | 15/207.2 |
| 6,031,147 A | 2/2000 | Gross | 604/359 |
| 6,107,358 A * | 8/2000 | Harada et al. | 521/133 |
| 6,229,062 B1 | 5/2001 | Mandell et al. | 604/367 |
| 6,248,274 B1 | 6/2001 | Williams | 264/103 |
| 6,353,146 B1 | 3/2002 | Williams | 604/359 |
| 6,656,913 B1 * | 12/2003 | Resheski-Wedepohl et al. | 514/25 |
| 6,743,965 B2 * | 6/2004 | Yang et al. | 604/367 |
| 6,803,496 B2 * | 10/2004 | Elder et al. | 604/367 |
| 2005/0154133 A1 * | 7/2005 | Engelhardt et al. | |

FOREIGN PATENT DOCUMENTS

| | | |
|---|---|---|
| JP | 61-209658 | 9/1986 |
| JP | 03-193137 | 8/1991 |
| JP | 05-277148 | 10/1993 |
| JP | 06-54880 | 3/1994 |
| JP | 2001-29384 | 2/2001 |
| WO | WO81/01643 | 6/1981 |
| WO | WO 99/32706 | 7/1999 |
| WO | WO 99/61079 A1 | 12/1999 |
| WO | WO0051655 A1 * | 9/2000 |
| WO | WO 00/66187 | 11/2000 |

OTHER PUBLICATIONS

U.S. Statutory Invention Registration H1579 to Furio, published Aug. 6, 1996.
U.S. Statutory Invention Registration H1732.
Canadian Office Action dated Aug. 2, 2011 for corresponding Canadian Patent Application No. 2,443,668.

* cited by examiner

*Primary Examiner* — Lynne Anderson
(74) *Attorney, Agent, or Firm* — Ohlandt, Greeley, Ruggiero & Perle, L.L.C.

(57) ABSTRACT

There is provided a tampon or similar device or product in which there is disposed at least one surface active agent. A broad feature of the present invention provides a fibrous absorbent article for absorbing body fluids made up of a fibrous material defining a structure suitable for absorbing the body fluids, and disposed in or on the structure, an effective amount of at least one surface active agent, so as to adsorb malodor associated with these bodily fluids.

8 Claims, No Drawings

US 8,093,446 B2

FIBROUS ABSORBENT ARTICLES HAVING MALODOR COUNTERACTANT

BACKGROUND OF THE INVENTION

1. Field of the Invention

The present invention relates to fibrous absorbent articles having a surface active agent with odor adsorbing properties. More particularly, the present invention relates to fibrous absorbent articles with at least one surface active agent that has the ability to adsorb onto surfaces or interfaces to alter the surfaces or interfacial free energy of the interfaces of the fibrous absorbent articles, where the interfacial free energy is defined as the force needed to oppose the pull of the molecules in the surface or interface.

2. Description of the Prior Art

A variety of proposals have been made in the past as a way to counteract menstrual odors. Such proposals include the use of perfumes to mask the odors that emanate from the absorbent article. Other proposals include the use of substances to suppress or remove odoriferous compounds that may be generated in the presence of menstrual fluids and the like. These odoriferous compounds may be suppressed by a number of mechanisms including forming a non-odoriferous compound by chemical reaction or by absorption of the odoriferous compounds into a solid or liquid. For an absorbent to be effective in deodorizing, especially for odors from body fluids that are characterized as having very low olfactory thresholds, it is essential that the sorbent be capable of removing, in its environment, virtually all the odoriferous compounds regardless of the concentration thereof.

In order to provide a full background for the present invention reference may be made to U.S. Pat. Nos. 3,948,257; 4,795,482; 4,826,497; 5,364,380; and also Registration H1579.

U.S. Pat. No. 3,948,257 is directed to a vulva deodorant system comprising a tampon for insertion into the vagina and a device for retaining a deodorant. The device includes a deodorant in the form of a perfume, powder or the like.

U.S. Pat. No. 4,795,482 is directed to a process for eliminating odors and compositions for use therein. The method involves reducing the odors below olfactory detection by contact of the odor producing species with a synthetic crystalline siliceous molecular sieve material.

U.S. Pat. No. 4,826,497 provides fibrous absorption articles having enhanced deodorizing properties by having disposed therein an effective amount of crystalline siliceous molecular sieve having pore diameters of at least about 5.5 angstroms and a relatively low capacity for adsorbed water. In addition, this patent provides for the inclusion of zeolite particles having a size of less than about 20 micrometers in the deodorizing sieve. The particles are positioned between the exterior surface of the fluid permeable cover of the absorbent article and a baffle provided within the article.

U.S. Pat. No. 5,364,380 provides an absorbent article having a first surface facing the body of a user and a second surface aligned approximately opposite to the first surface. There is also provided a liquid-impermeable baffle and a fluid-permeable cover positioned adjacent to the respective surfaces. In addition, a deodorizing mixture is positioned in the article to remain dry for a substantial period of time. The mixture is an anhydrous, non-buffer blend of at least basic and pH neutral odor adsorbing particles.

Registration H1579 provides zeolites having "intermediate" $SiO_2/Al_2O_3$ ratios used in catamenials, diapers and the like to control odors. Such intermediate ratios are described as typically in the range from about 2 to about 10.

It may be the case that when applied appropriately there are particular benefits and advantages to the several inventions described in the aforesaid patents. However, it will be apparent that the present invention provides a key advantage not found in prior art. What has been discovered and recognized is that the fibrous absorbent articles with the at least one surface active agent of the present invention have the capacity to adsorb odoriferous organic molecules on or in the fibrous absorbent article and in the bodily fluid in the vagina. As a result, malodor is controlled and/or eliminated.

SUMMARY OF THE INVENTION

It is an object of the present invention to provide a fibrous absorbent catamenial article or product, such as a tampon, that can be reliably and inexpensively produced and that will efficiently adsorb odors associated with menstrual fluid.

It is another object of the present invention to provide such a tampon having at least one surface active agent with odor adsorbing properties.

It is yet another object of the present invention to provide such a tampon where the at least one surface active agent adsorbs onto the surface or interface to alter the surface or interfacial free energy of the interface, resulting in odor adsorption.

It is a further object of the present invention to provide a method of incorporating the at least one surface active agent into a tampon.

The above and other objects and advantages of the present invention are achieved by a tampon or similar device or product in which there is disposed at least one surface active agent. Briefly stated, a broad feature of the present invention is a fibrous absorbent article for absorbing body fluids made up of a fibrous material defining a structure suitable for absorbing the body fluids, and disposed in or on the structure, an effective amount of at least one surface active agent, so as to adsorb malodor associated with these bodily fluids.

Other and further objects, advantages and features of the present invention will be understood by reference to the following description.

DETAILED DESCRIPTION OF THE INVENTION

The present invention is directed to a fibrous absorbent article, such as a tampon or feminine pad, with at least one surface active agent disposed on or in the fibrous absorbent article. The at least one surface active agent has the property of adsorbing onto surfaces or interfaces to alter the surface or interfacial free energies of the interface. The term "interface", as used herein, refers to a boundary between phases including, but not limited to, liquid-liquid phase boundaries, liquid-solid phase boundaries, liquid-gas phase boundaries, and gas-solid phase boundaries. When vaginal malodor compositions come into contact with a fibrous absorbent article, such as a tampon, the phase boundary area between the malodor and fiber surface is large relative to the volume of the system. Therefore, the total mass of the system is present at the boundaries.

The behavior of the fiber system is determined to a large degree by the interfacial processes. The at least one surface active agent can play an important role in the process. Surface active agents have a molecular structure with a structural group that has little attraction for the solvent phase (lyophobic) and a group that has a strong attraction for the solvent phase (lyophilic). When surface active agents are added to the surface of fibers of a tampon, the presence of the lyophobic group causes a distortion of the solvent liquid structure, thus increasing the free energy of the system. In the presence of an aqueous solution of a surface active agent, this distortion of the malodor (water) phase by the lyophobic group, and the resulting increase in the free energy of the system, results in less energy required to bring a surface active agent, rather than a water molecule, to the surface. Therefore, the at least one surface active agent concentrates on the surface of the fibrous absorbent article.

The presence of the lyophilic group prevents the surface active agent from being expelled from the solvent phase. As a result, the surface active agent concentrates at the surface and orients itself so that the hydrophilic group is in the aqueous phase (malodor phase) and the hydrophobic group is oriented away from the aqueous phase. The malodorous components are therefore chemically bound (ionic and/or covalent) by the surface active agents onto the surface at the fiber-liquid interface.

The chemical structure of the at least one surface active agent suitable for this application can vary with the nature of the fiber chemistry, malodor phase and the conditions of use. In the presence of a polar solvent phase such as vaginal malodor, ionic or highly polar groups may act as the lyophilic groups. In the presence of electrolytes or organic additives as in vaginal malodor, several surface active agents may be needed to maintain surface activity at a suitable level. For surface activity (adsorption of malodor) to be effective, the at least one surface active agent molecule must have a chemical structure that is amphipathic in the malodor phase under the conditions of use.

Suitable surface active agents for use with the present invention include, but are not limited to, one or more surfactants, polymers, or any combinations thereof.

Suitable surfactants include, but are not limited to, one or more anionic, nonionic, cationic, amphoteric, silicone-based, polymeric, or any combinations thereof.

Suitable anionic surfactants that may be used in the present invention include, but are not limited to, sodium alkyl aryl ethoxy sulfate, alkylalkoxylated phosphate ester sodium salt, dioctylester of sodium sulfosuccinic acid, dioctyl sulfosuccinate, ammonium salt of polycarboxylic acid, potassium salt of complex organic phosphate ester, ammonium lauryl ether sulfate, or any combinations thereof.

Suitable nonionic surfactants that may used in the present invention include, but are not limited to, polyoxyethylene, polyoxyethylene stearic acid, polyoxyethylene 40 hydrogenated castor oil, alkanolamides, isostearyl alcohol, polyoxyethylene /polyoxypropylene block copolymer, glycerol mono/dioleate, glycerol mono/distearate, ethoxylated linear alcohols (50% ethoxylated), PEG-2 stearate, polyoxyalkylated isostearyl alcohol, polyoxyethylene sorbitan monostearate, triglycerol monooleate, polysorbate 80, glyceryl monostearate, diglyceryl diisostearate, polyoxyethylene 20, polyoxyethylene 20 sorbitan monooleate, silicone glycol copolymer, polyglyceryl ester, glycol distearate, ethoxylated alcohols (Ceteareth-20), glycol esters (PEG 400 ditallate), or any combinations thereof.

Suitable cationic surfactants that may be used in the present invention include, but are not limited to, trimethyl coco quaternary ammonium chloride, distearyl dimonium chloride, benzalkonium chloride, benzethonium chloride, or any combinations thereof.

Suitable amphoteric surfactants that may be used in the present invention include, but are not limited to, coconut-based (imidazoline, dicarboxylate, sodium salt), coco amido betaine, betaine derivatives (oleyl betaine), octyl dipropionate, cocamphoglycinate, or any combinations thereof.

Suitable silicone-based surfactants that may be used in the present invention include, but are not limited to, cetyl dimethicone copolyol, dialkoxy dimethyl polysiloxane, polysiloxane polyalkyl copolymers, or any combinations thereof.

Suitable polymer that may be used in the present invention includes, but is not limited to, acrylates/C10-30 alkyl acrylate crosspolymer.

In order to achieve the odor adsorption properties of the present invention, the at least one surface active agent is present in an amount about 0.001 percentage by weight (wt. %) to about 30 wt. % and preferably about 0.01 wt. % to about 5 wt. %, based on the total weight of the fibrous absorbent article.

The following example demonstrates the effectiveness of the use of a surface active agent on a tampon to reduce and/or eliminate malodor.

A study was conducted to identify and rate the aroma attributes and intensities of malodor treated non-deodorant tampons with varying levels/types of malodor adsorbing/neutralizing treatments, including one with a surface active agent according to the present invention.

Samples were prepared using unscented tampons according to a detailed protocol. Each sample included a 15% malodor applied to the unscented tampon. The samples prepared are indicated below in Table 1. The samples in Table 1 were prepared and tested on three separate occasions.

TABLE 1

| Samples | |
|---|---|
| Sample A | Non-deodorant tampon + 15% malodor solution |
| Sample B | Non-deodorant tampon + 15% malodor solution + zeolite (0.7 wt. % to 2.63 wt. %) |
| Sample C | Non-deodorant tampon + 15% malodor solution + glycerin (0.92 wt. % to 3.61 wt. %) |
| Sample D | Non-deodorant tampon + 15% malodor solution + glycerin (0.92 wt. % to 1.81 wt. %) + polyoxyethylene (20) (0.64 wt. % to 1.25 wt. %) |

Evaluation of the samples was performed in a well-ventilated room having an exhaust fan available. Five objective sensory experts, trained experienced, and calibrated in aroma analysis, evaluated the samples on the date of receipt. Each panelist received a complete set of samples with the control and non-deodorant products. All panelists evaluated a sample at the same time, and consensus results of the characteristics and intensities were recorded. Panelists waited at least 30 minutes between evaluations and were allowed to smell a neutral substrate (paper napkin or back of arm) between and within samples as needed to prevent acclimating to the malodor or fragrance. For each session, one sample was randomly repeated as a check of intensity results. The repeated sample was generally one for which variable results were detected within jar from a single sample treatment.

The intensity of the sensory characteristics were rated on a 15 point intensity scale with 0=none and 15=very strong. Data is reported as consensus data. It is noted that panelists are able to see small differences and can often detect aroma differences as small as 0.2 units on the 15-point scale used. Panelists commonly detect differences of 0.5 units.

Table 2 provides mean results over three replications. When reviewing Table 2, it is noted that for attributes having a range in intensity across jars within a sample, the highest values were used to calculate means.

TABLE 2

Non-Deodorant Samples - Mean Profiles

|  | Sample A MEAN | Sample B MEAN | Sample C MEAN | Sample D MEAN |
|---|---|---|---|---|
| Malodor Intensity | 6.0 | 5.9 | 5.3 | 4.9 |
| Isovaleric | 1.7 | 2.0 | 2.0 | 1.8 |
| Ammonia | 2.4 | 2.0 | 1.8 | 2.0 |
| Degraded Protein | 2.5 | 2.5 | 2.3 | 1.8 |
| Ferric | 1.0 | 1.0 | 1.0 | 0.9 |
| Popcorn/Paper | 0.0 | 0.2 | 0.0 | 0.3 |
| Sulfite/Paper | 0.8 | 0.0 | 0.0 | 0.3 |

As is evident from Table 2, Sample D, with the surface active agent according to the present invention, exhibited the lowest overall malodor intensity of the samples tested.

The at least one surface active agents may be incorporated in a fibrous absorbent article in any of the following methods, including but not limited to, application during fiber processing, post-processing fiber surface treatment, deposited on the inside of the article, applied to the exterior of the article, included in a coverstock material, included in the removal string or other removal device, included as part of the applicator, encapsulated and applied in above-referenced ways, or any combinations thereof. Application methods may include but are not limited to spraying of surfactant in a patterned or random arrangement, deposited in droplets, or any combinations thereof.

The present invention having been thus been described with particular reference to the preferred forms thereof, it will be obvious that various changes and modifications may be made therein without departing from the spirit and scope of the present invention as defined in the appended claims.

What is claimed is:

1. A tampon for absorbing malodor in a vagina consisting of:
a plurality of fibers that form a fibrous absorbent body, the fibrous absorbent body having an outer surface, and
an anionic surface active agent concentrated at said outer surface,
wherein said outer surface with said anionic surface active agent concentrated thereon forms an interface area between the fibrous absorbent body and the malodor,
wherein said interface area has an interfacial free energy that increases when said anionic surface active agent adsorbs malodor in the interface area,
wherein said anionic surface active agent is selected from the group consisting of sodium alkyl aryl ethoxy sulfate, alkylalkoxylated phosphate ester sodium salt, dioctylester of sodium sulfosuccinic acid, ammonium salt of polycarboxylic acid, potassium salt of complex organic phosphate ester, ammonium lauryl ether sulfate, and any combinations thereof, and
wherein said anionic surface active agent is present in the tampon in an amount about 0.001 wt. % to about 30 wt. %, based on a total weight of said tampon.

2. A tampon for absorbing malodor in a vagina consisting of:
a plurality of fibers that form a fibrous absorbent body, the fibrous absorbent body having an outer surface, and
a nonionic surface active agent concentrated at said outer surface,
wherein said outer surface with said nonionic surface active agent concentrated thereon forms an interface area between the fibrous absorbent body and the malodor,
wherein said interface area has an interfacial free energy that increases when said nonionic surface active agent adsorbs malodor in interface area,
wherein said nonionic surface active agent is selected from the group consisting of polyoxyethylene, polyoxyethylene stearic acid, polyoxyethylene 40 hydrogenated castor oil, alkanolamide, isostearyl alcohol, ethoxylated linear alcohols, PEG-2 stearate, polyoxyalkylated isostearyl alcohol, polyoxyethylene sorbitan monostearate, polysorbate 80, polyoxyethylene 20, polyoxyethylene 20 sorbitan monooleate, silicone glycol copolymer, glycol distearate, ethoxylated alcohol, glycol ester, and any combinations thereof, and
wherein said at least one nonionic surface active agent is present in the tampon in an amount about 0.001 wt. % to about 30 wt. %, based on a total weight of said tampon.

3. The tampon of claim 2, wherein said nonionic surface active agent is polyoxyethylene 20, and is present in an amount of between 0.64 wt % to 1.25 wt %, based on a total weight of the tampon.

4. A tampon for absorbing malodor in a vagina consisting of:
a plurality of fibers that form a fibrous absorbent body, the fibrous absorbent body having an outer surface, and
a silicone-based surface active agent concentrated at the outer surface,
wherein said outer surface with said silicone-based surface active agent concentrated thereon forms an interface area between the fibrous absorbent body and the malodor,
wherein said interface area has an interfacial free energy that increases when said silicone-based surface active agent adsorbs malodor in the interface area,
wherein said silicone-based surface active agent is selected from the group consisting of cetyl dimethicone copolyol, dialkoxy dimethyl polysiloxane, polysiloxane polyalkyl copolymer, and any combinations thereof, and
wherein said silicone-based surface active agent is present in the tampon in an amount about 0.001 wt. % to about 30 wt. %, based on a total weight of said tampon.

5. A tampon for absorbing malodor in a vagina consisting of a plurality of fibers that form a fibrous absorbent body, the fibrous absorbent body having an outer surface, and
an acrylates/C10-30 alkyl acrylate crosspolymer adsorbed thereon and concentrated at said outer surface,
wherein said outer surface with said acrylates/C10-30 alkyl acrylate crosspolymer concentrated at said outer surface forms an interface area between the fibrous absorbent body and the malodor,
wherein said interface area has an interfacial free energy that increases when said acrylates/C10-30 alkyl acrylate crosspolymer adsorbs onto the interface area, and
wherein said acrylates/C10-30 alkyl acrylate crosspolymer is present in the tampon in an amount about 0.001 wt. % to about 30 wt. %, based on a total weight of said tampon.

6. A method for counteracting vaginal malodor comprising the steps of:
providing a tampon having a plurality of fibers that form a fibrous absorbent body, the fibrous absorbent body having an outer surface that forms an interface area between the fibrous absorbent body and the malodor; and
disposing about 0.001 wt. % to about 30 wt. %, based on a total weight of said tampon, of at least one surface active agent on said tampon, wherein said at least one surface active agent is concentrated at said outer surface, the interface area having an interfacial free energy that increases when the at least one surface active agent adsorbs malodor in the interface area, wherein the vaginal malodor has one or more malodor molecules that are chemically bound by the at least one surface active agent onto the interface area, and wherein said surface active agent is selected from the group consisting of:

anionic surface active agent selected from the group consisting of sodium alkyl aryl ethoxy sulfate, alkylalkoxylated phosphate ester sodium salt, dioctylester of sodium sulfosuccinic acid, ammonium salt of polycarboxylic acid, potassium salt of complex organic phosphate ester, ammonium lauryl ether sulfate;

nonionic surface active agent selected from the group consisting of polyoxyethylene, polyoxyethylene stearic acid, polyoxyethylene 40 hydrogenated castor oil, alkanolamide, isostearyl alcohol, ethoxylated linear alcohols, PEG-2 stearate, polyoxyalkylated isostearyl alcohol, polyoxyethylene sorbitan monostearate, polysorbate 80, polyoxyethylene 20, polyoxyethylene 20 sorbitan monooleate, silicone glycol copolymer, glycol distearate, ethoxylated alcohol, glycol ester;

cationic surface active agent selected from the group consisting of distearyl dimonium chloride, benzethonium chloride;

amphoteric surface active agent selected from the group consisting of coconut-based imidazoline, coconut-based dicarboxylate, coconut-based sodium salt, betaine derivative, octyl dipropionate, cocamphoglycinate;

silicone-based surface active agent selected from the group consisting of cetyl dimethicone copolyol, dialkoxy dimethyl polysiloxane, polysiloxane polyalkyl copolymer; and any combinations of the above, wherein the tampon consists of said plurality of fibers and said surface active agent.

7. The method of claim 6, wherein said nonionic surface active agent is polyoxyethylene 20, and wherein between 0.64 wt % to 1.25 wt %, based on a total weight of the tampon, of said nonionic surface active agent is disposed on said tampon.

8. A method for counteracting vaginal malodor comprising the steps of:

providing a tampon having a plurality of fibers that form a fibrous absorbent body, the fibrous absorbent body having an outer surface that forms an interface area between the fibrous absorbent body and the malodor; and disposing about 0.001 wt. % to about 30 wt. %, based on a total weight of said tampon, of an acrylates/C10-30 alkyl acrylate crosspolymer on said tampon, wherein said acrylates/C10-30 alkyl acrylate crosspolymer is concentrated at said outer surface, the interface area having an interfacial free energy that increases when the acrylates/C10-30 alkyl acrylate crosspolymer is adsorbs malodor in the interface area, and wherein the vaginal malodor has one or more malodor molecules that are chemically bound by said acrylates/C10-30 alkyl acrylate crosspolymer onto the interface area, wherein the tampon consists of said plurality of fibers and said acrylates/C10-30 alkyl acrylate crosspolymer.

* * * * *